US007785567B2

(12) United States Patent
Ong et al.

(10) Patent No.: US 7,785,567 B2
(45) Date of Patent: Aug. 31, 2010

(54) GROWTH HORMONE-RELEASING PEPTIDES IN THE TREATMENT OR PREVENTION OF ATHEROSCLEROSIS AND HYPERCHOLESTEROLEMIA

(75) Inventors: Huy Ong, Ville Mont-Royal (CA); Sylvie Marleau, Rosemère (CA); André Tremblay, Laval-des-Rapides (CA)

(73) Assignees: Valorisation-Recherche, Société en Commandite, Montréal (CA); Valorisation HSJ, Société en Commandite, Montréal (CA)

( * ) Notice: Subject to any disclaimer, the term of this patent is extended or adjusted under 35 U.S.C. 154(b) by 238 days.

(21) Appl. No.: 10/525,266

(22) PCT Filed: Aug. 21, 2003

(86) PCT No.: PCT/GB03/03669

§ 371 (c)(1),
(2), (4) Date: Apr. 25, 2006

(87) PCT Pub. No.: WO2004/017986

PCT Pub. Date: Mar. 4, 2004

(65) Prior Publication Data

US 2006/0241054 A1 Oct. 26, 2006

Related U.S. Application Data

(60) Provisional application No. 60/467,890, filed on May 5, 2003.

(30) Foreign Application Priority Data

Aug. 23, 2002 (CA) .................................. 2399548

(51) Int. Cl.
*A61K 49/00* (2006.01)
*A01K 38/00* (2006.01)
*C07K 4/00* (2006.01)
(52) U.S. Cl. .............................. 424/9.1; 514/2; 530/329
(58) Field of Classification Search ........................ None
See application file for complete search history.

(56) References Cited

U.S. PATENT DOCUMENTS

| 4,411,890 A | 10/1983 | Momany |
| 6,025,471 A | 2/2000 | Deghenghi |
| 6,559,289 B1 | 5/2003 | Rudling et al. |
| 2003/0129663 A1 | 7/2003 | McGregor et al. |

FOREIGN PATENT DOCUMENTS

| WO | WO 89/07110 | 8/1989 |
| WO | WO 89/07111 | 8/1989 |
| WO | WO 93/04081 | 3/1993 |
| WO | WO 96/15148 | 5/1996 |
| WO | WO 98/22124 | 5/1998 |
| WO | WO 00/09537 | 2/2000 |
| WO | WO 00/23097 | 4/2000 |
| WO | WO 00/67770 | 11/2000 |
| WO | 01/94952 A2 | 12/2001 |

OTHER PUBLICATIONS

Imbimbo et al. European Journal of Clinical Pharmacology, 46: 421-425, Jun. 1994.*
Broglio et al. European Journal of Pharmacology, 448:193-200, May 10, 2002.*
Imbimbo et al. European Journal of Clinical Pharmacology, 46: 421-425, May 1994.*
American Heart Association (AHA), Heart and Stroke Statistics—2002 Update.*
Avallone et al., "Growth Hormone-Releasing Peptides as Novel Regulators of the PPAR-LXR-ABC Cascade," Poster Presentation at ENDO 2003, Philadelphia, PA, Abstract #P3-275 (Jun. 19-22, 2003).
Bodart et al., "CD36 Mediates the Cardiovascular Action of Growth Hormone-Releasing Peptides in the Heart," *Cir. Res.* 90:844-849 (2002).
Bodart et al., "Identification and Characterization of a New Growth Hormone-Releasing Peptide Receptor in the Heart," *Circ. Res.* 85:796-802 (1999).
Bowers et al., "On the in Vitro and in Vivo Activity of a New Synthetic Hexapeptide that Acts on the Pituitary to Specifically Release Growth Hormone," *Endocrinology* 114(5):1537-1545 (1984).
Bowers et al., "Structure-Activity Relationships of a Synthetic Pentapeptide that Specifically Releases Growth Hormone in Vitro," *Endocrinology* 106(3):663-667 (1980).
Bowers, "GH Releasing Peptides—Structure and Kinetics," *J. Pediatr. Endocrinol.* 6:21-31 (1993).
Bowers, "Growth Hormone-Releasing Peptide (GHRP)," *Cell. Mol. Life Sci.* 54:1316-1329 (1998).
Bowers, "Xenobiotic Growth Hormone Secretagogues: Growth Hormone Releasing Peptides," *Xenobiotic Growth Hormone Secretagogues*, Springer-Verlag, New York; Eds. Bereu, B. & Walker, R.F., Chapter 2, pp. 9-28 (1996).
Broglio et al., "Effects of Acute Hexarelin Administration on Cardiac Performance in Patients with Coronary Artery Disease During By-Pass Surgery," *Eur. J. Pharmacology* 448:193-200 (2002).

(Continued)

*Primary Examiner*—John D Ulm
*Assistant Examiner*—Stacey MacFarlane
(74) *Attorney, Agent, or Firm*—Nixon Peabody LLP

(57) ABSTRACT

According to the invention there is provided a method of treatment or prophylaxis of atherosclerosis, hypercholesterolemia or a cardiovascular disease associated with atherosclerosis, which method comprises administration of one or more Growth Hormone Releasing Peptides (GHRPs) to a patient in need of such treatment or prophylaxis. There are also provided methods of reducing blood plasma cholesterol levels, as well as methods of modulating the expression of the scavenger receptor CD36 and genes involved in cellular cholesterol efflux.

10 Claims, 10 Drawing Sheets

OTHER PUBLICATIONS

Bujold et al., "Growth Hormone-Releasing Peptides (GHRPs) Treatment Modulated Plasma Lipid Profile and the Scavenger Receptor Expression Within Macrophages," Presented at AFPC Conference 2003, Montreal, Canada, Abstract #A30 (May 29-Jun. 1, 2003).

Camanni et al., "Growth Hormone-Releasing Peptides and Their Analogs," *Front. Neuroendocrinol.* 19:47-72 (1998).

Chawla et al., "A PPARγ-LXR-ABCA1 Pathway in Macrophages Is Involved in Cholesterol Efflux and Atherogenesis," *Molecular Cell* 7:161-171 (2001).

Chawla et al., "PPAR-γ Dependent and Independent Effects on Macrophage-Gene Expression in Lipid Metabolism and Inflammation," *Nature Med.* 7(1):48-52 (2001).

Chinetti et al., "PPAR-α and PPAR-γ Activators Induce Cholesterol Removal from Human Macrophage Foam Cells Through Stimulation of the ABCA1 Pathway," *Nature Med.* 7(1):53-58 (2001).

Chisolm III et al., "The Oxidation of Lipoproteins by Monocytes-Macrophages," *J. Biol. Chem.* 274(37):25959-25962 (1999).

Colonna et al., "Cardiac Ischemia and Impairment of Vascular Endothelium Function in Hearts from Growth Hormone-Deficient Rats: Protection by Hexarelin," *Eur. J. Pharmacol.* 334:201-207 (1997).

De Winther & Hofker, "Scavenging New Insights Into Atherogenesis," *J. Clin. Invest.* 105(8):1039-1041 (2000).

Deghenghi et al., "Small Peptides as Potent Releasers of Growth Hormone," *J. Ped. End. Metab.* 8:311-313 (1995).

Deghenghi, "Growth Hormone Releasing Peptides," *Xenobiotic Growth Hormone Secretagogues*, Springer-Verlag, New York; Eds. Bereu, B. & Walker, R.F., Chapter 6, pp. 85-102 (1996).

Deghenghi, "The Development of 'Impervious Peptides' as Growth Hormone Secretagogues," *Acta Paediatr. Suppl.* 423:85-87 (1997).

Demers et al., "Détermination du Site de Liaison de L'Hexaréline sure le Récepteur Scavenger CD36," Presented at AFPC Conference 2003, Montreal, Canada, Abstract #A26 (May 19-23, 2003).

Demers et al., "Determination of Hexarelin Binding Domain on the Scavenger Receptor CD36," Poster Presentation at ENDO 2003, Philadelphia, PA, Abstract #P2-225 (Jun. 19-22, 2003).

Dickson et al., "Systemic Administration of Growth Hormone-Releasing Peptide Activates Hypothalamic Arcuate Neurons," *Neuroscience* 53(2):303-306 (1993).

Febbraio et al., "CD36: A Class B Scavenger Receptor Involved in Angiogenesis, Atherosclerosis, Inflammation, and Lipid Metabolism," *J. Clin. Invest.* 108(6):785-791 (2001).

Febbraio et al., "Targeted Disruption of the Class B Scavenger Receptor CD36 Protects Against Atherosclerotic Lesion Development in Mice," *J. Clin. Invest.* 105(8):1049-1056 (2000).

Feng et al., "Induction of CD36 Expression by Oxidized LDL and IL-4 by a Common Signaling Pathway Dependent on Protein Kinase C and PPAR-γ," *J. Lipid Res.* 41:688-696 (2000).

Gayet, "L'essential de 1999 dans la maladie coronaire," *Arch. Des Maladies Du Coeur et des Vaisseaux* 93(1 Spec No):51-59 (2000).

Ghigo et al., "Endocrine and Non-Endocrine Activities of Growth Hormone Secretagogues in Humans," *Horm. Res.* 51(Suppl. 3):9-15 (1999).

Ghigo et al., "Growth Hormone-Releasing Peptides," *Eur. J. Endocrinol.* 136:445-460 (1997).

Glass & Witztum, "Atherosclerosis: The Road Ahead," *Cell* 104:503-516 (2001).

Hegyi et al., "Macrophage Death and the Role of Apoptosis in Human Atherosclerosis," *J. Hematotherapy & Stem Cell Res.* 10:27-42 (2001).

Hodel, "Myopathy and Rhabdomyolysis with Lipid-Lowering Drugs," *Toxicol. Lett.* 128:159-168 (2002).

Huber et al., "Interleukin-6 Exacerbates Early Atherosclerosis in Mice," *Arterioscler. Thromb. Vasc. Biol.* 19:2364-2367 (1999).

Janabi et al., "Oxidized LDL-Induced NF-κB Activation and Subsequent Expression of Proinflammatory Genes Are Defective in Monocyte-Derived Macrophages From CD36-Deficient Patients," *Arterioscler. Thromb. Vasc. Biol.* 20:1953-1960 (2000).

Kiechl et al., "The Natural Course of Atherosclerosis. Part I: Incidence and Progression," *Arterioscler. Thromb. Vasc. Biol.* 19:1484-1490 (1999).

Kojima et al., "Purification and Distribution of Ghrelin: The Natural Endogenous Ligand for the Growth Hormone Secretagogue Receptor," *Horm. Res.* 56(Suppl. 1):93-97 (2001).

Lau et al., "Severe Rhabdomyolysis Associated with the Cerivastatin-Gemfibrozil Combination Therapy," *Texas Heart Institute J.* 28(2):142-145 (2001).

Maor et al., "Oxidized Monocyte-Derived Macrophages in Aortic Atherosclerotic Lesion from Apolipoprotein E-Deficient Mice and from Human Carotid Artery Contain Lipid Peroxides and Oxysterols," *Biochem. Biophys. Res. Commun.* 269:775-780 (2000).

Marleau et al., "Effect of Growth Hormone Releasing Peptides (GHRPs) on Monocyte/Macrophage Scavenger Receptors (SR) B (CD36) Expression and Monocyte Trafficking," *Inflammation Research* 50(Supplement 3):S154 (2001), Presented at Fifth World Congress of Inflammation, Edinburgh, Scotland, Abstract #06/02 (Sep. 22-26, 2001).

Marleau et al., "Growth Hormone Releasing Peptides as a New Therapy for Atherosclerosis," Sixth International Inflammation Conference, Vancouver, Canada, Abstract (Aug. 2003).

Momany et al., "Conformational Energy Studies and in Vitro and in Vivo Activity Data on Growth Hormone-Releasing Peptides," *Endocrinology* 114(5):1531-1536 (1984).

Momany et al., "Design, Synthesis, and Biological Activity of Peptides which Release Growth Hormone in Vitro," *Endocrinology* 108(1):31-39 (1981).

Moore et al., "The Role of PPAR-γ in Macrophage Differentiation and Cholesterol Uptake," *Nature Med.* 7(1):41-47 (2001).

Nagy et al., "Oxidized LDL Regulates Macrophage Gene Expression through Ligand Activation of PPARγ," *Cell* 93:229-240 (1998).

Nakata et al., "CD36, a Novel Receptor for Oxidized Low-Density Lipoproteins, Is Highly Expressed on Lipid-Laden Macrophages in Human Atherosclerotic Aorta," *Arterioscler. Thromb. Vasc. Biol.* 19:1333-1339 (1999).

Nicholson et al., "CD36 in Atherosclerosis. The Role of a Class B Macrophage Scavenger Receptor," *Ann. New York Acad. Sci.* pp. 128-133 (2000).

Nicholson et al., "Oxidized LDL Binds to CD36 on Human Monocyte-Derived Macrophages and Transfected Cell Lines," *Arterioscler. Thromb. Vasc. Biol.* 15:269-275 (1995).

Nozaki et al., "Reduced Uptake of Oxidized Low Density Lipoproteins in Monocyte-Derived Macrophages from CD36-Deficient Subjects," *J. Clin. Invest.* 96:1859-1865 (1995).

Ong et al., "Growth Hormone-Releasing Peptides as Inhibitors of Fatty Streaks Formation: A New Therapy for Atherosclerosis," Poster Presentation at ENDO 2003, Philadelphia, PA, Abstract #P2-223 (Jun. 19-22, 2003).

Ong et al., "Growth Hormone-Releasing Peptides as Negative Modulators of Atherosclerosis and Hypercholesterolemia," Presented at Fourth Symposium on Growth Hormone Secretagogues, Tampa, FL (Nov. 7-10, 2002).

Ong et al., "Physiological Function of Growth Hormone Secretagogue Receptors in the Cardiovascular System," *Peptides and Non-Peptides of Oncologic and Neuroendocrine Relevance: From Basic to Clinical Research*, Springer-Verlag, Ed.: Müller, E.E., Chapter 12, pp. 117-127 (2003).

Podrez et al., "Macrophage Scavenger Receptor CD36 is the Major Receptor for LDL Modified by Monocyte-Generated Reactive Nitrogen Species," *J. Clin. Invest.* 105(8):1095-1108 (2000).

Rosenfeld et al., "Advanced Atherosclerotic Lesions in the Innominate Artery of the ApoE Knockout Mouse," *Arterioscler. Thromb. Vasc. Biol.* 20:2587-2592 (2000).

Rossoni et al., "Protectant Activity of Hexarelin of Growth Hormone Against Postischemic Ventricular Dysfunction in Hearts from Aged Rats," *J. Cardiovasc. Pharmacol.* 32:260-265 (1998).

Schoen et al., "Section IV. Immunology, Endocrinology and Metabolic Diseases," *Ann. Rep. Med. Chem.* 28:177-186 (1993).

Silverstein & Febbraio, "CD36 and Atherosclerosis," *Curr. Opin. Lipidol.* 11:483-491 (2000).

Tremblay et al., "Growth Hormone-Releasing Peptides as Novel Regulators of the Nuclear Receptor PPARgamma in Macrophage," Presented at FEBS 2003, Brussels, Belgium, Abstract #537 (Jul. 3-8, 2003).

Veeraragavan et al., "Growth Hormone-Releasing Peptide (GHRP) Binding to Porcine Anterior Pituitary and Hypothalamic Membranes," *Life Sci.* 50:1149-1155 (1992).

Walker et al., "Effects of Stimulated Growth Hormone Secretion on Age-Related Changes in Plasma Cholesterol and Hepatic Low Density Lipoprotein Messenger RNA Concentrations," *Mechanisms of Ageing and Development* 75:215-226 (1994).

Wang et al., "Effect of Growth Hormone Releasing Peptides on Fatty Streak Formation and Lipid Uptake by Macrophages in Apolipoprotein E Deficient (APOE −/−) Atherosclerotic Mice," Presented at AFPC Conference 2003, Montreal, Canada, Abstract #A26 (May 29-Jun. 1, 2003).

Widimský & Anděl, "Prevalence of Coronary Atherosclerosis in Asymptomatic Population," *Eur. Heart J.* 21:13-14 (2000).

Wright et al., "Analysis of Serious Adverse Events," *Can. Fam. Phys.* 48:486-489 (2002).

Broglio et al., "Effects of Acute Hexarelin Administration on Cardiac Performance in Patients with Coronary Artery Disease During By-Pass Surgery," *European Journal of Pharmacology* 448(2-3):193-200 (2002).

Walker et al., "Effects of Stimulated Growth Hormone Secretion on Age-Related Changes in Plasma Cholesterol and Hepatic Low Density Lipoprotein Messenger RNA Concentrations," *Mechanisms of Ageing and Development* 75(3):215-226 (1994).

Marleau et al., "Effect of Growth Hormone Releasing Peptides (GHRPs) on Monocyte/Marcophage Scavenger Receptors (SR) B (CD36) Expression and Monocyte Trafficking," *Inflammation Research* 50(SUPP 3):S154 (2001).

Bodart et al., "CD35 Mediates the Cardiovascular Action of Growth Hormone-Releasing Peptides in the Heart," *Circulation Research* 90(8):844-849 (2002).

* cited by examiner

ApoE-null mice, 12 weeks treatment with GHRPs

*, $p < 0.01$ and **, $p < 0.001$ compared with 0.9% NaCl; #, $p < 0.05$ compared with HEX ApoE null mice, 12 weeks treatment with GHRPs

*, p < 0.01 compared with 0.9% NaCl; #, p < 0.01 compared with HEX

*, p < 0.01 compared with 0.9% NaCl; #, p < 0.01 compared with HEX

A: 8 weeks (from 10 to 18 weeks of age) treatment with EP80317 or 0.9% NaCl solution.

B: 6 weeks (from 12 to 18 weeks of age) treatment with EP80317 or 0.9% NaCl solution.

C: 4 weeks (from 14 to 18 weeks of age) treatment with EP80317 or 0.9% NaCl solution.

The symbols * and ** indicate $P<0.05$ and $P<0.02$, respectively, compared to vehicle.

SEQUENCE LISTING

```
<160> NUMBER OF SEQ ID NOS: 8

<210> SEQ ID NO 1
<211> LENGTH: 6
<212> TYPE: PRT
<213> ORGANISM: artificial
<220> FEATURE:
<223> OTHER INFORMATION: Hexarelin
<220> FEATURE:
<221> NAME/KEY: MISC_FEATURE
<222> LOCATION: (1)..(1)
<223> OTHER INFORMATION: D-isomer
<220> FEATURE:
<221> NAME/KEY: MISC_FEATURE
<222> LOCATION: (2)..(2)
<223> OTHER INFORMATION: methylation
<220> FEATURE:
<221> NAME/KEY: MISC_FEATURE
<222> LOCATION: (4)..(4)
<223> OTHER INFORMATION: D-isomer
<220> FEATURE:
<221> NAME/KEY: MISC_FEATURE
<222> LOCATION: (6)..(6)
<223> OTHER INFORMATION: amination

<400> SEQUENCE: 1

His Trp Ala Trp Phe Lys
1               5

<210> SEQ ID NO 2
<211> LENGTH: 6
<212> TYPE: PRT
<213> ORGANISM: artificial
<220> FEATURE:
<223> OTHER INFORMATION: EP80317
<220> FEATURE:
<221> NAME/KEY: MISC_FEATURE
<222> LOCATION: (1)..(1)
<223> OTHER INFORMATION: HAIC D-isomer (5-amino-1,2,4,5,6,7-tetrahydro-
      azepino[3,2,1-hi]indole-4-one-2-carboxylic acid)
<220> FEATURE:
<221> NAME/KEY: MISC_FEATURE
<222> LOCATION: (2)..(2)
<223> OTHER INFORMATION: D-isomer
<220> FEATURE:
<221> NAME/KEY: MISC_FEATURE
<222> LOCATION: (2)..(2)
<223> OTHER INFORMATION: methylation
<220> FEATURE:
<221> NAME/KEY: MISC_FEATURE
<222> LOCATION: (4)..(4)
<223> OTHER INFORMATION: D-isomer
<220> FEATURE:
<221> NAME/KEY: MISC_FEATURE
<222> LOCATION: (6)..(6)
```

```
<223> OTHER INFORMATION: amination

<400> SEQUENCE: 2

Xaa Trp Lys Trp Phe Lys
1               5

<210> SEQ ID NO 3
<211> LENGTH: 22
<212> TYPE: DNA
<213> ORGANISM: artificial
<220> FEATURE:
<223> OTHER INFORMATION: LXRalpha forward PCR primer

<400> SEQUENCE: 3
cctgtcagaa gaacagatcc gc                                          22

<210> SEQ ID NO 4
<211> LENGTH: 23
<212> TYPE: DNA
<213> ORGANISM: artificial
<220> FEATURE:
<223> OTHER INFORMATION: LXRalpha reverse PCR primer

<400> SEQUENCE: 4
tcttcagcag ggcaatctgg tcc                                         23

<210> SEQ ID NO 5
<211> LENGTH: 22
<212> TYPE: DNA
<213> ORGANISM: artificial
<220> FEATURE:
<223> OTHER INFORMATION: ABCA1 forward PCR primer

<400> SEQUENCE: 5
ggtcaatgga aggttcaggt gc                                          22

<210> SEQ ID NO 6
<211> LENGTH: 26
<212> TYPE: DNA
<213> ORGANISM: artificial
<220> FEATURE:
<223> OTHER INFORMATION: ABCA1 reverse PCR primer

<400> SEQUENCE: 6
ggagtcgctt tttgctctgg gagagg                                      26

<210> SEQ ID NO 7
<211> LENGTH: 24
<212> TYPE: DNA
<213> ORGANISM: artificial
<220> FEATURE:
<223> OTHER INFORMATION: GAPDH forward PCR primer

<400> SEQUENCE: 7
ggtcttactc cttggaggcc atgt                                        24

<210> SEQ ID NO 8
<211> LENGTH: 25
<212> TYPE: DNA
<213> ORGANISM: artificial
<220> FEATURE:
<223> OTHER INFORMATION: GAPDH genotype PCR primer

<400> SEQUENCE: 8
gaccccttca ttgacctcaa ctaca                                       25
```

GROWTH HORMONE-RELEASING PEPTIDES IN THE TREATMENT OR PREVENTION OF ATHEROSCLEROSIS AND HYPERCHOLESTEROLEMIA

This application is a national stage application under 35 U.S.C. §371 from PCT Application No. PCT/GB2003/003669, filed Aug. 21, 2003, which claims the priority benefit of Canadian Patent Application No. 2,399,548, filed Aug. 23, 2002, and U.S. Provisional Patent Application No. 60/467,890, filed May 5, 2003.

FIELD OF THE INVENTION

The present invention relates to the use of Growth Hormone Releasing Peptides (GHRPs) in the treatment of and prophylaxis of atherosclerosis, hypercholesterolemia and related diseases.

BACKGROUND AND PRIOR ART

Atherosclerosis is a multifactorial disease developing preferentially in subjects presenting biochemical risks factors including smoking, hypertension, diabetes mellitus, hypercholesterolemia, elevated plasma low density lipoprotein (LDL) and triglycerides, hyperfibrinogenemia and hyperglycemia, among others. Atherosclerotic lesions develop over a number of decades in humans, leading to complications such as coronary and cerebral ischemic and thromboembolic diseases and myocardial and cerebral infarction. To date, cardiovascular disease is the leading cause of morbidity and mortality in industrialised countries and progresses steadily in emerging countries, with coronary atherosclerosis being the main underlying pathology. Currently, therapy of atherosclerosis is not completely efficient to prevent disease development and complication.

Atherosclerosis develops through the sequential interplay of at least three pathological processes: foam cell differentiation, inflammatory reaction and cell proliferation.

In humans and in various animal models, one of the earliest detectable events in the first of these processes is the recruitment of mononuclear phagocytes and lymphocytes to the intact endothelial lining of large arteries. Enhanced adhesion and accumulation of blood monocytes into the intima is then accompanied by a change in cell phenotype, where they transform into macrophages. The latter engulfs lipids and stores them as cytoplasmic droplets, thus becoming "foam cells". The formation of such foam cells is a key stage in the development of early fatty streak lesions, and hence is a central event in atherogenesis.

The type B scavenger receptor CD36, which is known to have multiple functions, is recognised to play a key role in scavenging oxidized low density lipoproteins into monocytes/macrophages.

Growth hormone releasing peptides (GHRPs), which consist of a family of small synthetic peptides modelled from Met-enkephalin, possess potent and dose dependent growth hormone-releasing activity and significant prolactin and corticotropin-releasing effects (see *Horm. Res.* 51(suppl. 3), 9 (1999)).

The neuroendocrine activities of GHRPs are mediated by a specific G protein-coupled receptor identified as Ghrelin receptor expressed in hypothalamus and pituitary gland (see *Horm. Res.* 56(suppl. 1), 93 (2001)). However, GHRPs also provide a cardioprotective effect against cardiac ischemia in growth hormone (GH) deficient or aged rats. This protective activity is not coupled to any apparent stimulation of the somatotropic function, suggesting a direct myocardial action of these peptides (see *Eur. J. Pharmacol.* 334, 201 (1997)).

A study of GHRP binding sites in the cardiovascular system found that hexarelin, a hexapeptide member of the GHRP family, binds to a glycosylated membrane protein of 84 kD distinct from the Ghrelin receptor (see *Circ. Res.* 85, 796 (1999)). This protein was later identified as the CD36 receptor (see *Circ. Res.* 90, 844 (2002)).

None of the above-mentioned prior art suggests that GHRPs, or their synthetic analogues, can be employed to inhibit the lipid-scavenging function of the receptor CD36, thereby providing utility in the treatment and prevention of atherosclerosis, hypercholesterolemia and related diseases.

DISCLOSURE OF THE INVENTION

The present inventors have found that a prolonged treatment (12 weeks) with GHRPs interferes with the CD36 scavenger receptor function and expression, thereby reducing the uptake of oxidised LDL (oxLDL) and the accumulation of lipids and cholesterol, and consequently, reducing the formation of fatty streak lesions in ApoE-null mice.

The ApoE-null mouse was selected as an experimental model of atherosclerosis as it features the progressive series of atherogenic events seen in human, including increased adhesive interactions between leukocyte and endothelium, conversion of monocyte-derived macrophages into foam cells with lesions distributing throughout the arterial tree, and late development of more advanced lesions (fibrous plaques).

ApoE-null mice show very high levels of plasma cholesterol as a result of impaired clearance of cholesterol-enriched lipoproteins and, as for humans, high fat high cholesterol (HCHF) diet exacerbates disease progression and markedly enhances plasma cholesterol levels (see *J. Clin. Invest.* 105 (8), 1049-1056 (2000) and *J. Clin. Invest.* 105, 1039-1041 (2000)). Evidence accumulates to support that fatty streaks in anatomical sites prone to atheromatous plaque development precede mature lesions in humans, although all fatty streaks do not progress to atheromas (see *Arterioscler. Thromb. Vasc. Biol.* 19, 2364-2367 (1999)). In both human and mice, T lymphocyte and foam cells are found in fatty streaks and immunological processes have been shown to be similar over the years in both species.

The present inventors have found that GHRPs reduce total plasma cholesterol and non-HDL cholesterol, and increase HDL cholesterol in ApoE-deficient mice fed with a HFHC diet from 6 weeks old. These favourable changes in plasma lipids were associated with a significant decrease in fatty streak lesion area in the ApoE-null mice treated with GHRPs, as compared with controls.

The present inventors have also found that GHRPs regulate CD36 expression in peritoneal macrophages from ApoE-null mice in mice fed a HFHC diet for 12 weeks.

The present inventors have further found using cultured macrophages from differentiated monocytic THP-1 cells, that treatment with GHRPs contributes to decrease lipid storage in macrophages, with a concomitant increase in gene expression of nuclear receptor LXRα and ABCA1 transporter, two proteins involved in cellular cholesterol efflux.

GHRPs therefore appear to prevent cholesterol accumulation in macrophages and foam cell formation, thereby reducing fatty streak development. Although not wishing to be bound by theory, it is for this reason that the present inventors believe that GHRPs may be efficient to prevent the development of atherosclerotic plaques and cardiovascular disease linked to atherosclerotic processes such as coronary artery disease, myocardial infarction and strokes.

Thus, according to a first aspect of the present invention, there is provided a method of treatment or prophylaxis of atherosclerosis or hypercholesterolemia, thereby preventing the development of and/or treating a cardiovascular disease associated with atherosclerosis, which method comprises administration of one or more GHRPs to a patient in need of such treatment or prophylaxis.

The term "cardiovascular disease associated with atherosclerosis" includes references to diseases that are medically linked to atherosclerosis in that they are a consequence of atherosclerotic lesions. Cardiovascular diseases associated with atherosclerosis that may be mentioned include coronary artery disease, myocardial infarction and strokes.

In one embodiment of the first aspect of the invention, there is provided a method of preventing the development of atherosclerotic plaques, hypercholesterolemia or a cardiovascular disease associated with atherosclerosis, which method comprises the administration of one or more GHRPs to a patient at risk of developing such plaques, hypercholesterolemia or cardiovascular diseases. This embodiment of the invention encompasses treatment of patients with GHRPs in order to prevent the formation of atherosclerotic plaques or their precursors (e.g. fatty streaks).

Without wishing to be bound by theory, it is believed that this embodiment of the invention prevents fatty streak formation and atherosclerosis development through modulating negatively CD36 expression in macrophages, which leads to inhibition of oxLDL internalization, thus breaking the cycle of foam cell formation and the feed-forward loop of oxLDL-induced PPARγ and CD36 expression (see *Nature Med.* 7, 41-47 (2001)), in addition to reducing total plasma cholesterol and non-HDL cholesterol.

In a second embodiment of the first aspect of the invention, there is provided a method of treating pre-existing atherosclerosis or hypercholesterolemia, thereby treating and/or preventing the development of a cardiovascular disease associated with atherosclerosis, which method comprises administration of one or more GHRPs to a patient who has atherosclerosis, hypercholesterolemia and/or a cardiovascular disease associated with atherosclerosis. This embodiment of the invention encompasses treatment of patients with GHRPs in order to reduce the size of pre-existing atherosclerotic plaques or their precursors (e.g. fatty streaks).

According to a second aspect of the invention, there is provided a method of reducing the total blood plasma cholesterol level of a patient in need of such cholesterol level reduction, which method comprises administering to said patient one or more GHRPs. In one embodiment of this method, GHRPs are administered to the patient in order to reduce plasma levels of non-HDL cholesterol.

According to a third aspect of the invention, there is provided a method of negatively modulating (reducing) CD36 expression, which method comprises administering one or more GHRPs to a patient who would benefit from negative modulation of CD36 expression.

In a preferred embodiment of this aspect of the invention, there is provided a method of negatively modulating CD36 expression in (monocyte-derived) macrophages, which method comprises administering one or more GHRPs to a patient who would benefit from such negative modulation of CD36 expression in macrophages.

According to a fourth aspect of the invention, there is provided a method of increasing expression of genes involved in cellular cholesterol efflux, which method comprises administering one or more GHRPs to a patient who would benefit from increased expression of such genes.

Genes involved in cellular cholesterol efflux that may be mentioned include those for nuclear receptor LXRα and ABCA1 transporter.

Decreased expression of CD36 and increased expression of LXRα and ABCA1 transporter may take place simultaneously. As such, an embodiment of the invention relates to a method of modulating the key regulators of net cellular flux of cholesterol (e.g. to and from macrophages), by negative modulation of CD36 expression and/or function and by increasing expression of genes involved in cellular cholesterol efflux, which method comprises administering one or more GHRPs to a patient who would benefit from such modulation of net cellular cholesterol flux. As will be appreciated by those skilled in the art, negative modulation of CD36 expression and/or function results in reduced uptake of oxLDL by scavenger receptor CD36.

When used herein, the term "expression", unless otherwise indicated, refers to the production of mRNA by transcription of the relevant gene and/or, particularly, to production of protein via gene transcription and then mRNA translation. Similarly, the term "expression of genes" refers to production of protein via gene transcription and then mRNA translation and/or, particularly, to the production of mRNA by transcription of the relevant gene.

Patients:
(i) in need of blood cholesterol level reduction;
(ii) who would benefit from negative modulation of CD36 expression;
(iii) who would benefit from increased expression of genes involved in cellular cholesterol efflux; and
(iv) who would benefit from reduced uptake of oxLDL by scavenger receptor CD36 and from increased expression of genes involved in cellular cholesterol efflux include those that have blood cholesterol levels that are likely to cause or exacerbate cardiovascular disease or dysfunction. Such patients include:
(a) those having coronary heart disease and those at risk of developing it because of multiple risk factors (including obesity, smoking, hypertension, diabetes mellitus and a family history of premature coronary heart disease);
(b) those with familial conditions characterised by very high plasma concentrations of cholesterol and/or triglycerides;
(c) those with hyperlipidemia not secondary to underlying diseases (such as hypothyroidism, nephrotic syndrome, hepatic disease or alcholoism);
(d) those with elevated LDL-cholesterol; and
(e) those under dietary hypolipidemic intervention (complementary treatment).

When used herein, the term "GHRPs" includes references to (synthetic) peptide compounds that can activate the pituitary-hypothalamus axis (see *Neuroscience* 53, 303 (1993)) and act directly on the pituitary somatotroph by a non-Growth Hormone Releasing Hormone (non-GHRH), non-opiate and non-somatostatin secretory pathway. The term also includes references to structurally related (peptidomimetic) compounds that are: (a) capable of inhibiting GH release by other GHRPs and themselves have no effect on GHRH agonism; and/or (b) devoid of GH-releasing activity and have no effect on GHRH agonism. Examples of GHRPs (including their antagonists) are described in: "*Xenobiotic Growth Hormone Secretagogues*", Eds. B. Bercu & R. F. Walker, pp. 9-28 and 85-102, Springer-Verlag, New York (1996); *J. Ped. End. Metab.* 8, 311-313 (1996); *Acta Paediatr. Suppl.* 423, 85-87 (1997); *Life Sci.* 50, 1149-1155 (1992); *Eur. J. Endocrinol.* 136, 445-460 (1997); *J. Pediatr. Endocrinol.* 6, 21-31 (1993); *Ann. Rep. Med. Chem.* 28, 177-186 (1993); *Endocrinology*

106, 663-667 (1980); ibid. 108, 31-39 (1981); ibid. 114, 1531-1536 and 1537-1545 (1984); *Front. Neuroendocrinol.* 19(1), 47-72 (1998); *Cell. Mol. Life Sci.* 54(12), 1316-1329 (1998); WO 89/07110; WO 89/07111; WO 93/04081; WO 96/15148; U.S. Pat. Nos. 4,411,890; and 6,025,471.

In respect of all of the above-mentioned aspects of the invention, GHRPs that may be mentioned include those of the hexarelin (HEX) family, such as HEX (His-(D) -(Me)Trp-Ala-Trp-(D)-Phe-Lys-NH$_2$, SEQ ID NO: 1) and EP80317 (Haic-(D) -(Me)Trp-(D)-Lys-Trp-(D)-Phe-Lys-NH$_2$, SEQ ID NO: 2), the latter peptide being devoid of GH-secreting activity in vivo. Preferred GHRPs include Hexarelin and EP80317. Particularly preferred GHRPs include those, like EP80317, that are devoid of GH-secreting activity in vivo.

The methods of the present invention, such as the method of the first aspect of the invention, preferably include the step of systemic administration of GHRP to afford a protective amount of drug in circulation. In a most specific embodiment, Hexarelin, EP80317 and any GHRP analog is exogenously administered. The methods of the present invention may be used to treat animals or, preferably, humans.

Further aspects of the present invention include methods according to any of the above-mentioned aspects of the invention, except that, in place of GHRPs, related synthetic analogs of HEX and EP80317 and any ligands which bind to the receptor(s) of those compounds or of GHRPs are employed. Ligands which bind to the receptor(s) of GHRPs include CD36 ligands, which may be identified using in silico techniques involving molecular modelling of the (GHRP) binding site on CD36.

Further aspects of the invention also include:
1) The use of growth hormone releasing peptides of Hexarelin family, of derived peptidomimetics and of CD36 ligands in the prevention and treatment of atherosclerosis and hypercholesterolemia.
2) The use of GHRP derivatives, of derived peptidomimetics, and of CD36 ligands which modulate the expression of scavenger receptor B (CD36) in the prevention of the development of atherosclerotic lesions and in the prevention of heart attacks and strokes associated with coronary artery disease and hypercholesterolemia.
3) The use of GHRP derivatives and of derived peptidomimetics which modulate the expression of the ATP-binding cassette ABCA1 transporter and scavenger receptor B (CD36) in the prevention of the development of atherosclerotic lesions and in the prevention of heart attacks and strokes associated with coronary artery disease and hypercholesterolemia.
4) A pharmaceutical composition containing a compound as defined in points 1) to 3) above, to be administered exogenously.

In one embodiment of aspect 1) above, there is provided the use of growth hormone releasing peptides of Hexarelin family, of derived peptidomimetics as CD36 ligands in the prevention and treatment of atherosclerosis and hypercholesterolemia.

Further, in an embodiment of aspect 3) above, there is provided the use of GHRP derivatives and of derived peptidomimetics which modulate the expression of the ATP-binding cassette ABCA1 transporter in the prevention of the development of atherosclerotic lesions and in the prevention of heart attacks and strokes associated with coronary artery disease and hypercholesterolemia.

In the treatment of atherosclerosis, hypercholesterolemia or cardiovascular diseases associated with atherosclerosis, GHRPs may be administered in combination with other agents that have different mechanisms of action and that have beneficial effects on blood lipid levels.

Thus, in a yet further aspect of the invention there is provided a combination product comprising:
(i) a GHRP; and
(ii) an agent that produces beneficial effects on blood lipid levels, wherein each of components (i) and (ii) is formulated in admixture with a pharmaceutically-acceptable adjuvant, diluent or carrier.

The combination product according to this aspect of the invention provides for the administration of a GHRP in conjunction with an agent that produces beneficial effects on blood lipid levels, and may thus be presented either as separate formulations, wherein at least one of those formulations comprises a GHRP and at least one comprises an agent that produces beneficial effects on blood lipid levels, or may be presented (i.e. formulated) as a combined preparation (i.e. presented as a single formulation including a GHRP and an agent that produces beneficial effects on blood lipid levels).

Thus, there is further provided:
(1) a pharmaceutical formulation including a GHRP and an agent that produces beneficial effects on blood lipid levels, in admixture with a pharmaceutically-acceptable adjuvant, diluent or carrier; and
(2) a kit of parts comprising components:
   (a) a pharmaceutical formulation including a GHRP in admixture with a pharmaceutically-acceptable adjuvant, diluent or carrier; and
   (b) a pharmaceutical formulation including an agent that produces beneficial effects on blood lipid levels in admixture with a pharmaceutically-acceptable adjuvant, diluent or carrier, which components (a) and (b) are each provided in a form that is suitable for administration in conjunction with the other.

When used herein, the term "an agent that produces beneficial effects on blood lipid levels" includes references to pharmaceutically-active agents that are not GHRPs and that, upon administration to patients, have the effect of lowering of total cholesterol and/or triglyceride levels in the blood, of lowering of LDL cholesterol levels in the blood and/or of increasing HDL cholesterol levels in the blood. As such, this term includes references to any of the following active agents:
(I) statins (i.e. inhibitors of 3-hydroxy-3-methylglutaryl-coenzyme A (HMG-CoA) reductase), such as atorvastatin, cerivastatin, fluvastatin, lovastatin, mevastatin, pravastatin, rosuvastatin and simvastatin;
(II) fibrates (i.e. derivatives of fibric acids and related compounds), such as beclobrate, bezafibrate, ciprofibrate, clinofibrate, clofibrate, clofibride, etofylline clofibrate, fenofibrate, gemfibrozil, pirifibrate, plafibride, simfibrate and tocofibrate;
(III) bile-acid binding resins, such as colesevelam, colestipol, colestyramine and divistyramine;
(IV) nicotinates (i.e. nicotinic acid and its derivatives), such as acipimox, binifibrate, etofibrate, niceritrol, nicofibrate, pirozadil, ronifibrate, sorbinicate and tocoferil nicotinate;
(V) omega-3-triglycerides, such as omega-3-acid ethyl esters and omega-3-marine triglycerides;
(VI) acyl-coenzyme A:cholesterol O-acyl transferase (ACAT) inhibitors, such as avasimibe;
(VII) PPARγ agonists, such as pioglitazone;
(VIII) cholesterol absorption inhibitors, such as ezetimibe; and
(IX) lipase inhibitors, such as orlistat.

Preferred agents that produces beneficial effects on blood lipid levels include statins, such as those specifically mentioned at (I) above.

It will be appreciated that this aspect of the invention includes embodiments where the combination product additionally comprises one or more further GHRPs and/or one or more further agents that produce beneficial effects on blood lipid levels. As for the essential components of the combination product, each further GHRP or agent that produces beneficial effects on blood lipid levels may be formulated separately or in combination with any one of the other components of the combination product.

This invention will be described herein below, referring to specific embodied examples and appended figures, which purpose is to illustrate the invention rather than limit its scope.

BRIEF DESCRIPTION OF THE DRAWINGS

Having thus generally described the invention, reference will now be made to the accompanying drawings, showing by way of illustration a preferred embodiment thereof, and in which.

GHRPs prevent fatty streak formation in ApoE deficient mice fed a HFHC diet for 12 weeks (from 6 weeks old). Effects of HEX (100 µg/kg per day) and of EP80317 (300 µg/kg per day), administered subcutaneously for 12 weeks (from 6 weeks old).

A: Lesion area (% of total aorta area) on ApoE-null mouse aortas were reduced by 28 and 51% following treatment with HEX and EP80317, respectively, as compared to controls treated with 0.9% NaCl. The open bar represents vehicle (0.9% NaCl) treated mice, the solid bar, HEX treatment and the cross-hatched bar, EP80317 treatment. Asterisk indicates P<0.05 (**, P <0.01) compared with vehicle, and # indicates P<0.05 compared with HEX.

B: Photograph of representative mice aortas from vehicle- (top), HEX-(middle) and EP80317-treated (bottom) ApoE-null mice stained with Oil Red O (obtained from Sigma-Aldrich).

FIG. 2

GHRPs reduced total plasma cholesterol and non-HDL cholesterol, and tended to increase HDL cholesterol in ApoE-null mice fed a HFHC diet for 12 weeks (from 6 weeks old). Total plasma cholesterol and non-HDL cholesterol were decreased by 30 and 31%, respectively, in EP80317-treated ApoE-null mice under HFHC diet as compared to controls. HDL cholesterol increased by 65 and 73% in ApoE-null mice under HFHC treated with HEX and EP80317, respectively.

A: Effects of 12 weeks treatment (from 6 weeks old) with 0.9% NaCl (open bar), HEX, 100 µg/kg per day (solid bar) or EP80317 300 µg/kg per day (cross-hatched bar) on total plasma cholesterol in mice fed a HFHC or a normal diet.

B: Effects of treatments on plasma triglycerides.

C: Effects of treatments on HDL cholesterol.

D: Effects of treatments on non-HDL cholesterol.

Asterisk indicates P<0.01 compared with vehicle, and # indicates P<0.01 compared with HEX.

FIG. 3

GHRPs reduced oxLDL-induced peritoneal macrophage accumulation in wild type and in ApoE-null mice fed a HFHC diet for 12 weeks (from 6 weeks old.

A: Effects of 12 weeks treatment (from 6 weeks old) with 0.9% NaCl (open bar), HEX, 100 µg/kg per day (solid bar) or EP80317, 300 µg/kg per day (cross-hatched bar) on oxLDL (250 µg i.p., <6 nmol MDA/mg lipoprotein)-induced accumulation of macrophages in the peritoneal cavity in wild type C57BL/6 mice and CD36-null mice fed a HFHC diet. Peritoneal macrophage accumulation in wild type mice tended to be reduced by 37%.

B: Effects of 12 weeks treatment (from 6 weeks old) with 0.9% NaCl (open bar), HEX, 100 µg/kg per day (solid bar) or EP80317, 300 µg/kg per day (cross-hatched bar) on oxLDL-induced accumulation of macrophages in the peritoneal cavity in ApoE-null mice fed either a HFHC or a normal diet. Peritoneal macrophage accumulation was reduced by 39% in mice fed a normal diet.

FIG. 4

Figure 4:
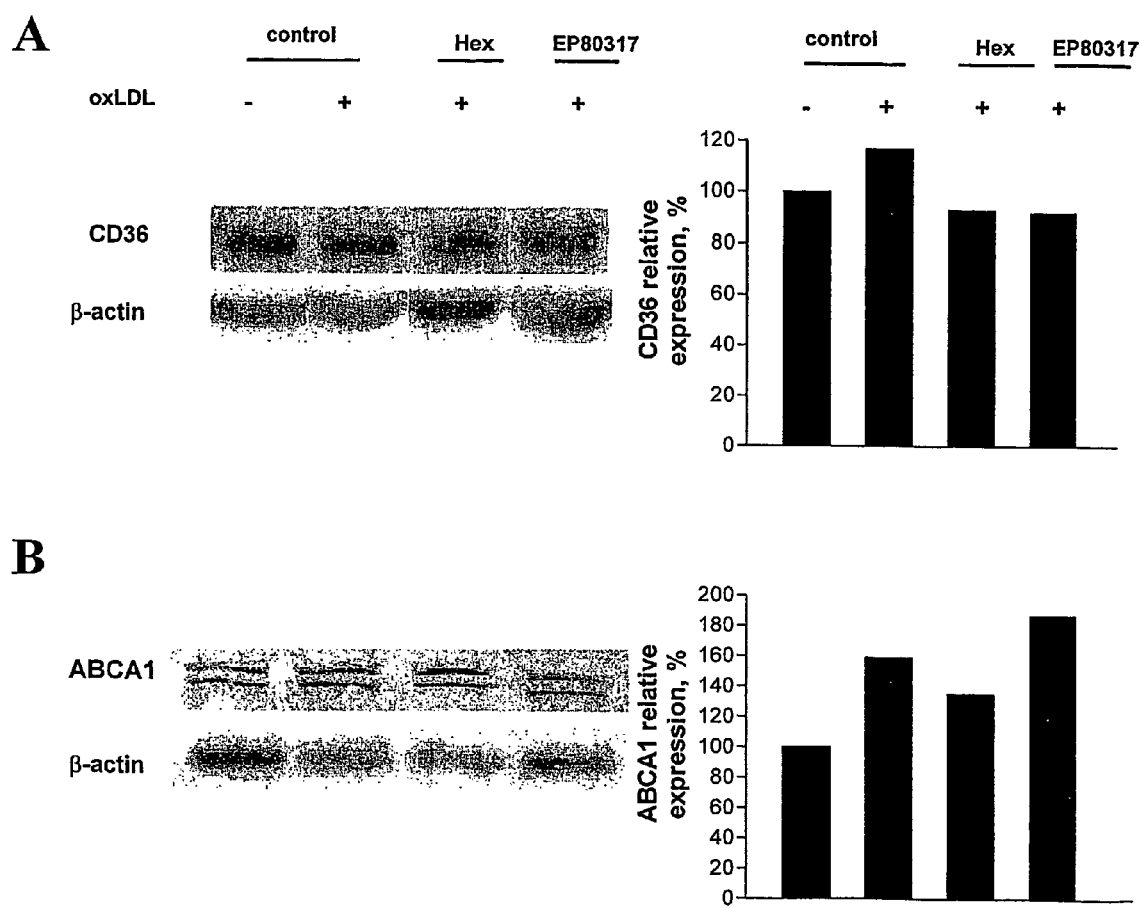

GHRPs modulate CD36 and ABCA1 protein levels in peritoneal macrophages from ApoE-null mice fed a HFHC diet for 12 weeks. FIG. 4 shows Western blot analysis on ox-LDL (250 µg i.p., <6 nmol MDA/mg lipoprotein)-elicited peritoneal macrophages collected from ApoE-null mice fed an HFHC diet and treated with GHRPs (either HEX, 100 µg/kg per day or EP80317, 300 µg/kg per day) for 12 weeks (from 6 weeks old). Relative protein levels for A, CD36 and B, ABCA1 are normalised to β-actin and expressed as % of change compared to vehicle (0.9% NaCl)-treated controls set at 100%. Data represent the mean of two independent experiments.

FIG. 5

GHRPs did not modulate the growth curve in ApoE-null mice fed a HFHC diet (or a normal diet) for 12 weeks (from 6 weeks old).

Effects of 12 weeks treatment (from 6 weeks old) with 0.9% NaCl (diamond), HEX, 100 µg/kg per day (square) or EP80317, 300 µg/kg per day (triangle) on weight of mice fed:

A: a HFHC diet; or

B: a normal diet.

FIG. 6

GHRPs did not modulate food intake in ApoE-null mice fed a HFHC diet (or a normal diet) for 12 weeks (from 6 weeks old).

Effects of 12 weeks treatment (from 6 weeks old) with 0.9% NaCl (diamond), HEX, 100 µg/kg per day (square) or EP80317, 300 µg/kg per day (triangle) on food intake in mice fed:

A: a HFHC diet; or

B: a normal diet.

FIG. 7

A: GHRPs reduce lipid accumulation in differentiated human macrophages. To induce lipid accumulation, human monocytic THP-1 cells were differentiated to macrophages with 5 ng/mL PMA for 48 hrs and then treated as indicated for 24 hrs with 10 µM HEX or EP80317 in the presence of phorbol myristate acetate (PMA). Non-differentiated cells (no PMA) were also analysed. Lipid accumulation was quantified by photometry at 510 nm following extraction of Oil Red O from stained cells. Lipid staining was reduced by 35% and 28% in macrophages treated with HEX and EP80317, respectively, compared to untreated cells.

B: GHRPs reduced lipid accumulation in peritoneal macrophages isolated from ApoE-null mice fed a HFHC diet from 13 to 18 weeks old. EP80317 (300 µg/kg) s.c. has been administered from 13 to 18 weeks old. Lipid staining (assessed by Oil Red O extraction) was reduced by 57% (compared to peritoneal macrophages isolated from ApoE-null mice fed a HFHC diet from 13 weeks old, but not treated with EP80317).

FIG. 8

GHRPs increase expression of genes involved in cellular cholesterol removal.

Figure 7A:
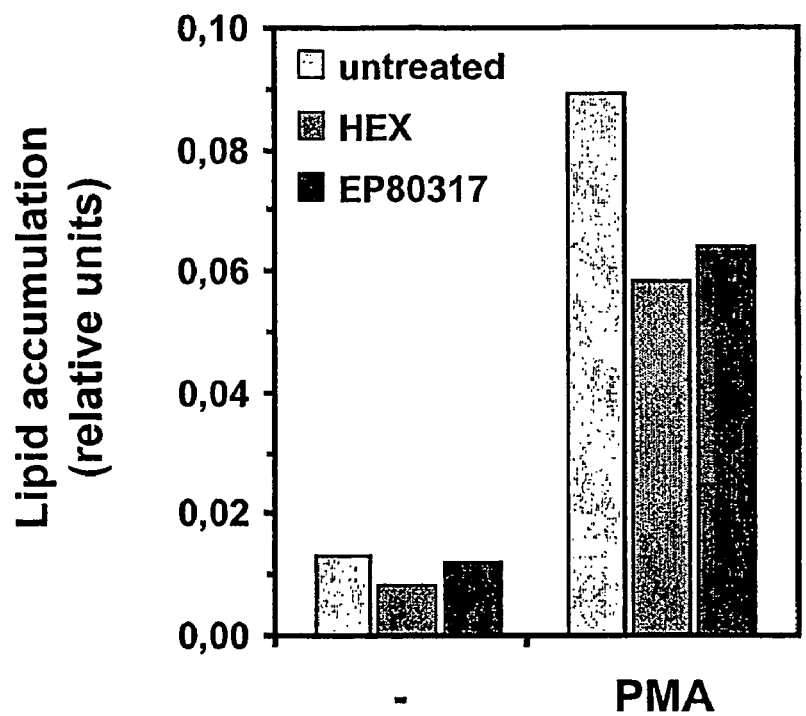
Figure 7B:
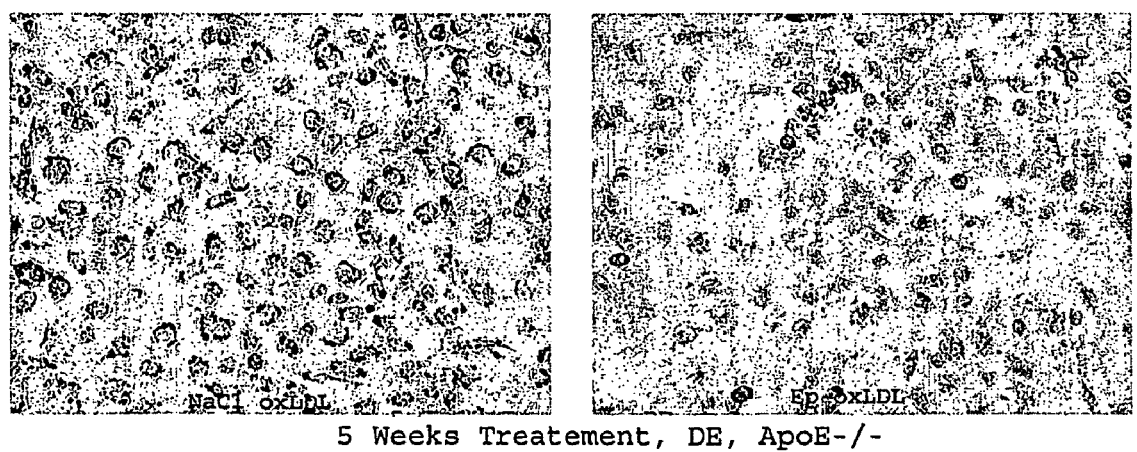
Figure 8:
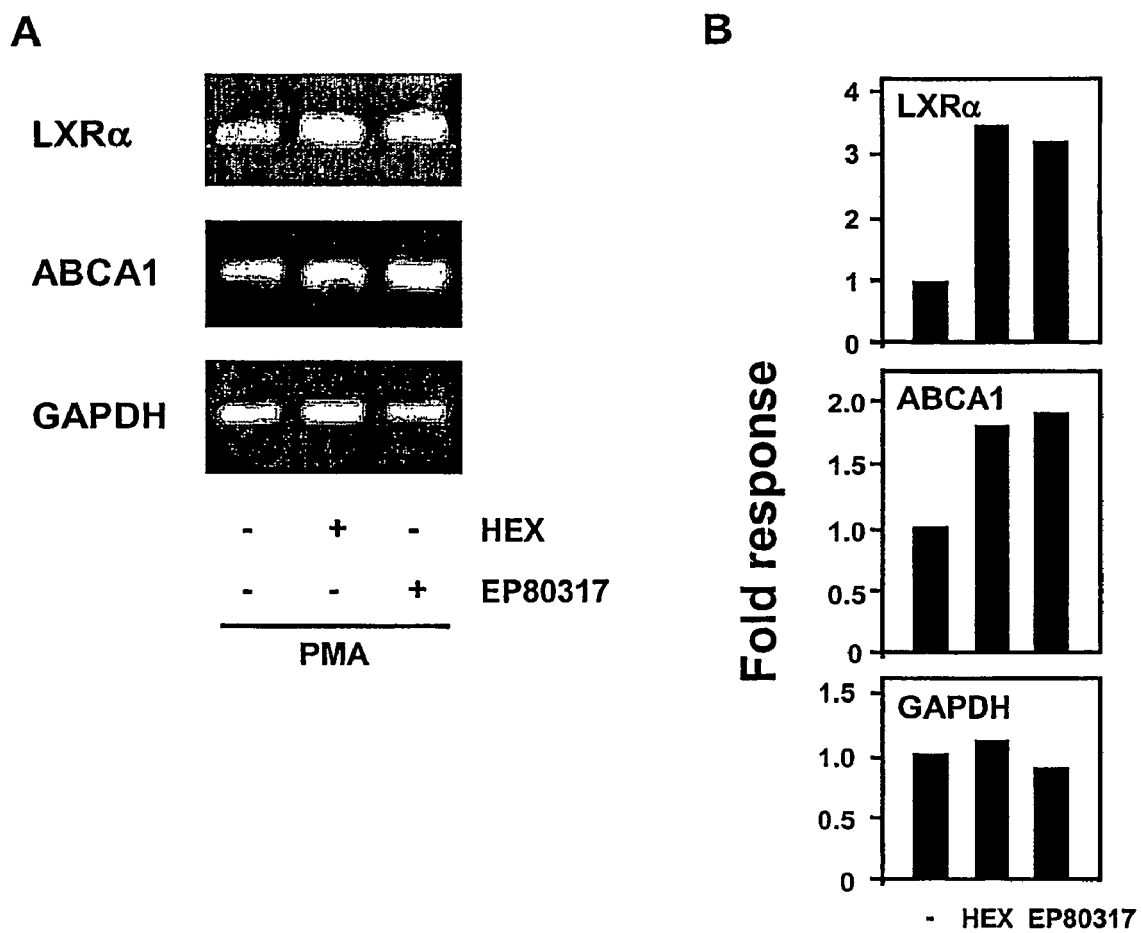

A: PMA-differentiated THP-1 macrophages were treated with HEX or EP80317 as described in relation to FIG. 7, and mRNA expression was analysed for selected genes by RT- PCR. The procedure involves extraction of total RNA from cells, which RNA is then reverse transcribed into cDNA and amplified in a PCR reaction with specific primers. Primers used are:

| | |
|---|---|
| LXRα forward | CCTGTCAGAAGAACAGATCCGC |
| LXRα reverse | TCTTCAGCAGGGCAATCTGGTCC; |
| ABCA1 forward | GGTCAATGGAAGGTTCAGGTGC |
| ABCA1 reverse | GGAGTCGCTTTTTGCTCTGGGAGAGG; |
| GAPDH forward | GGTCTTACTCCTTGGAGGCCATGT |
| GAPDH reverse | GACCCCTTCATTGACCTCAACTACA. |

B: Measurement of signal intensity from the experiment described in A was performed using an Alpha Imager analysis system and results expressed as fold response compared to untreated differentiated cells. GAPDH was used as a control for data normalisation.

FIG. 9

GHRPs prevent or delay the development or modulate the regression of fatty streaks in ApoE-null mice fed on a HFHC diet starting at 6 weeks of age for a period of 12 weeks.

The effects of EP80317 (300 μg/kg per day) administered subcutaneously for 8 weeks (from 10 to 18 weeks of age), 6 weeks (from 12 to 18 weeks of age) and 4 weeks (from 14 to 18 weeks of age) were documented, as well as the effect of hexarelin (100 μg/kg per day) given for 4 weeks (from 14 to 18 weeks of age).

A: Lesion area (% total aorta area) on ApoE-null aortas were reduced by 39.2% following treatment with EP80317 for 8 weeks as compared to controls treated with 0.9% NaCl.

B: Lesion area (% total aorta area) on ApoE-null aortas were reduced by 31.3% following treatment with EP80317 for 6 weeks as compared to controls treated with 0.9% NaCl.

C: Lesion area (% total aorta area) on ApoE-null aortas were reduced by 8% and 36% following treatment with hexarelin and EP80317, respectively, for 4 weeks as compared to controls treated with 0.9% NaCl.

Figure 9:
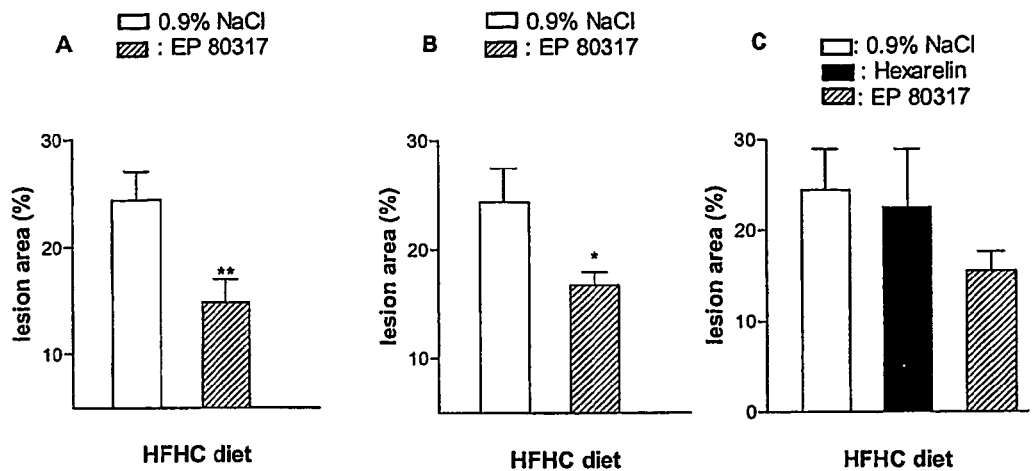

In FIG. 9, the open bars represent vehicle (0.9% NaCl) treated mice, the solid bar, hexarelin treatment and the cross-hatched bars, EP80317 treatment.

EXAMPLE 1

Growth Hormone-Releasing Peptides Prevent Fatty Streaks Formation

Severe morbidity results as a consequence of the arterial disease atherosclerosis and complications of the disease, such as myocardial infarction and strokes, remain a common cause of mortality in Western Society (see *J. Hematotherapy & Stem Cell Res.* 10(1), 27-42 (2001)). Current management strategies of atherosclerosis include life-style interventions such as healthy dietary and exercise recommendations and, mainly, the use of lipid lowering drug therapy, in addition to blood pressure control and use of antiplatelet drugs. Among hypolipemic drugs, hepatic hydroxymethylglutaryl-coenzyme A reductase inhibitors or statin drugs interfere with hepatic cholesterol metabolism which leads to a compensatory increase in LDL receptors and cholesterol clearance via these receptors. In contrast, fibrates and nicotinic acid mainly reduce circulating VLDL whereas bile acid binding resins interfere with bile acid reabsorption, thereby increasing fecal excretion of cholesterol. However, statins, used in monotherapy or in association with another lipid-lowering drug, have been associated with serious adverse effects, myopathy and rhabdomyolisis (see *Texas Heart Institute J.* 28, 142-145 (2001)). For instance, cerivastatin therapy has been associated with hundreds of myopathies and some dozens of deaths (see *Toxicol. Lett.* 128, 159-168 (2002)). Hence, use of these drugs should be revisited (see *Can. Fam. Phys.* 48, 486-489 (2002)).

To determine whether GHRPs reduce atherosclerosis development, we have used the ApoE deficient mice strain and their C57BL/6 control littermates to assess the effects of prolonged (12 weeks) GHRPs treatment on fatty streak formation in mice fed a an enriched lipid diet. The surface area of oil red-O staining aortas of mice has been used as an index of plaque development and changes in the plasma levels of lipids as an index of hypolipemic effect. Taken together, these end points served to evaluate the anti-atherosclerotic effect of GHRPs in vivo.

Methods

Drugs

HEX and EP80317 were a generous gift of Dr. R. Deghenghi, Europeptides, Argenteuil, France. HEX and EP80317 stock solutions were prepared in sterile 0.9% NaCl.

Animals

CD36-deficient and ApoE-deficient mice, as well as their control littermates were raised in the animal facilities of the Université de Montréal. The ApoE deficient mouse features the progressive series of atherogenic events seen in human, including increased adhesive interactions between leukocyte and endothelium, conversion of monocyte-derived macrophages into foam cells with lesions distributing throughout the arterial tree, and late development of more advanced lesions (fibrous plaques). ApoE-null mice show very high levels of plasma cholesterol as a result of impaired clearance of cholesterol-enriched lipoproteins and, as for humans, HCHF diet exacerbates disease progression and markedly enhances plasma cholesterol levels (see *J. Clin. Invest.* 105(8), 1049-1056 (2000) and *J. Clin. Invest.* 105, 1039-1041 (2000)). However, complex lesions as seen in humans are not observed except for the innominate artery in mice ~42 weeks old, where loss of continuity of the fibrous cap, rupture of xanthomas at the shoulders of lesions and intraplaque haemorrhage are seen (see *Arterioscler. Thromb. Vasc. Biol.* 20, 2587-2592 (2000)). Evidence accumulates to support that fatty streaks in anatomical sites prone to atheromatous plaque development precede mature lesions in humans, although all fatty streaks do not progress to atheromas (see *Arterioscler. Thromb. Vasc. Biol.* 19, 2364-2367 (1999)). In both human and mice, T lymphocyte and foam cells are found in fatty streaks and immunological processes have been shown to be similar over the years in both species.

The animals were housed in cages (less than 5 per cage) and fed a normal chow diet and water ad libitum. At 6 weeks of age, male C57BL/6, CD36 and ApoE-null mice were assigned to 1 of 3 groups (n=12 mice per group): Group 1 received daily injections of 0.9% NaCl (1 μL/g); Group 2, HEX (100 μg/kg, 1 μL/g), and Group 3, EP80317 (300 μg/kg, 1 μL/g). All three groups of mice were fed a HFHC diet (purchased from Research Diet Inc. (D.12108)) from 6 weeks of age. Daily s.c. treatment with HEX, EP80317 or vehicle was begun at 6 weeks old and continued for 12 weeks. Four days before sacrifice, 6 mice from Groups 1 to 3 were injected i.p. with oxLDL (minimally oxidized, 3-6 mmol/mg protein, as determined by Thiobarbituric Acid Reactive Substances (TBARS) assay). At 18 weeks old, mice were fasted overnight, anaesthetised with ketamine-xylazine (90:10 mg/kg)

two hours after the s.c. administration of the morning dose of the drug under study. Blood (1 mL) was taken from the heart and put into EDTA pre-coated microcontainers (BD, Franklin Lakes, N.J., USA). Mice were killed, the hearts were perfused with 20 mL 0.9% NaCl. The peritoneal cavity was washed with 3 mL of heparinised saline (10 units/mL) in mice injected i.p. with oxLDL. A hemacytometer and stained cytospin preparation (Diff Quick stain, Dade Diagnostics of P.R. Inc., Aguada, PR) were used to determine the total and differential leukocyte numbers, respectively, for the peritoneal cavity lavage fluid. The entire aorta from the heart, extending 5-10 mm after bifurcation of the iliac arteries and including the subclavian right and left common carotid arteries, was removed, dissected, and evaluated for lesion development by en face oil red-O staining and morphometry of scanned images using the software Scion Image (Scion Corp., Fredrick, Md.). The animal study protocol was reviewed and approved by the institutional Animal Ethics Committee of the Université de Montréal and conducted in accordance with the Canadian Council on Animal Care guidelines for use of experimental animals.

Plasma Lipid Analysis

Total plasma cholesterol, triacylglycerol and HDL cholesterol were determined using enzymatic kits (Sigma Chemicals). Appropriate standards and controls were included in each assay.

Statistical Analysis

Data are expressed as mean±SEM. Comparisons between groups were performed using a one-way analysis of variance (ANOVA) followed by pair-wise multiple comparisons using the Student-Newman-Keuls method. Differences were considered significant at $p<0.05$.

Results

Figure 1A:
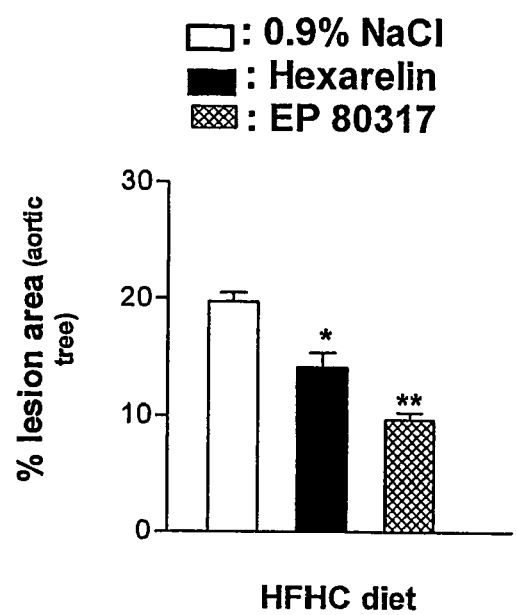
FIG. 1
Figure 1B:
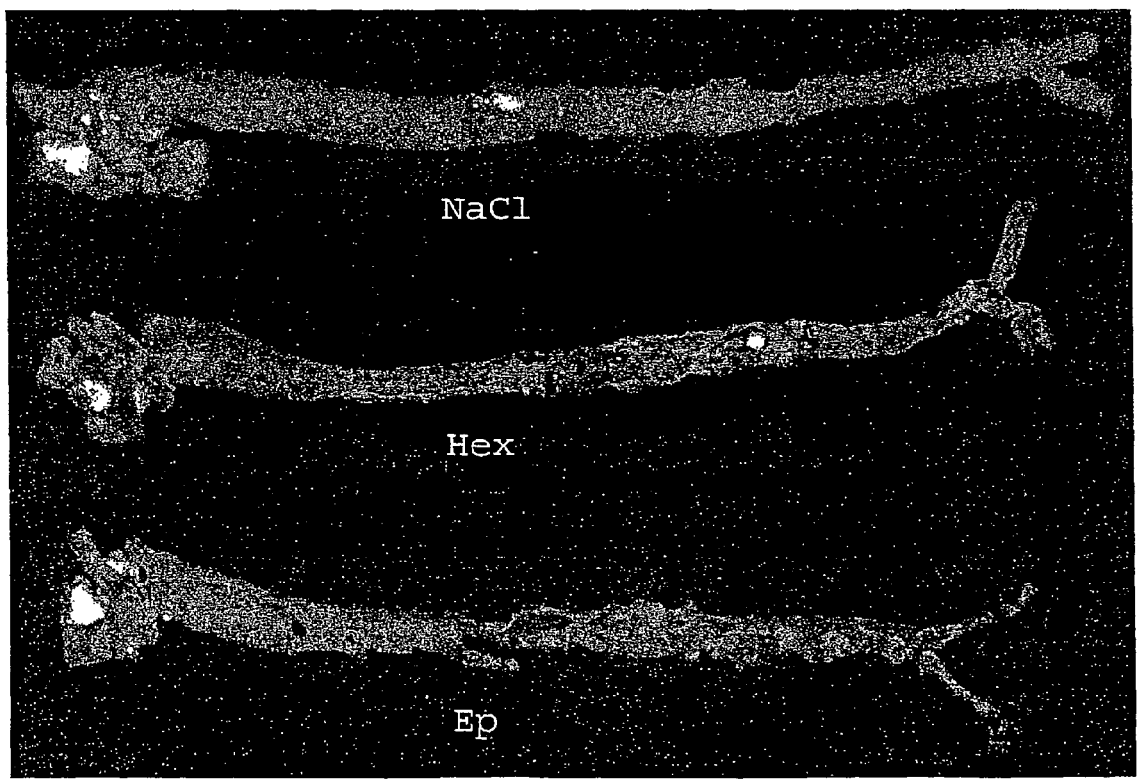

The most striking observation is a reduction of lesion area in ApoE-deficient mice, by 28 and 51% following treatment with HEX (100 µg/kg) and EP80317 (300 µg/kg) daily, respectively, in mice fed a HFHC diet (FIG. 1). CD36-deficient mice and their wild type C57BL/6 control littermates did not develop significant fatty streak lesions on HFHC diet (12 weeks, from 6 weeks old).

Figure 2:
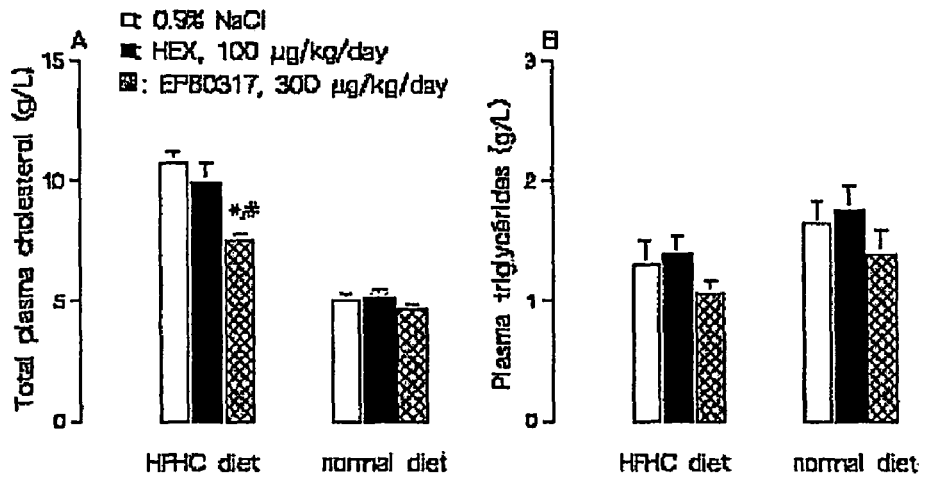
Figure 2:
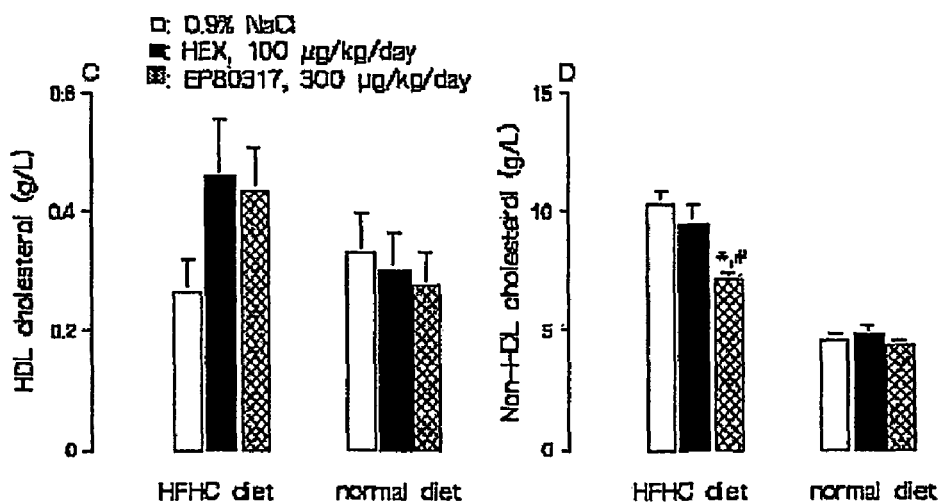

Reduced lesion area was accompanied with a decrease in total plasma cholesterol (30%), as well as in non-HDL plasma cholesterol (31%), in ApoE-deficient mice fed a HFHC diet and treated daily with EP80317 (300 µg/kg) daily for 12 weeks (from 6 weeks old), as compared to controls and to ApoE-null mice treated treated with HEX (100 µg/kg) daily (FIG. 2A and FIG. 2D). In contrast, HDL cholesterol tended to be increased in ApoE-null mice under HFHC diet (12 weeks, from 6 weeks old) treated with HEX (65%) or EP80317 (73%) as compared to (0.9% NaCl-administered) controls on HFHC diet (FIG. 2C). Plasma triglycerides did not change significantly (FIG. 2B). GHRPs did not modulate total plasma cholesterol levels in CD36-deficient or C57BL/6 controls fed, from 6 weeks old, a HFHC diet for 12 weeks (data not shown).

Figure 3:
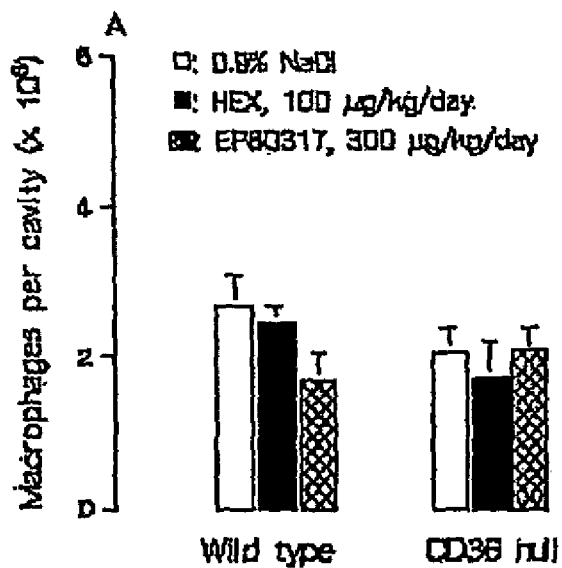
Figure 3:
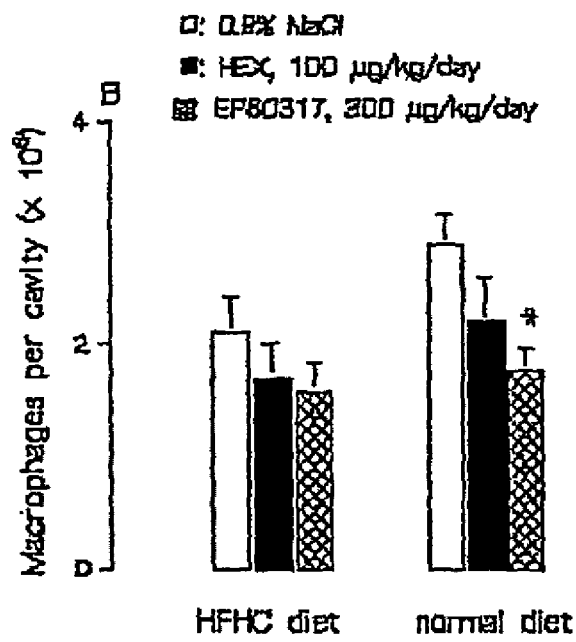

EP80317 reduced oxLDL-induced peritoneal macrophage accumulation by 37% and 39%, respectively, in wild type C57BL/6 mice fed a HFHC diet and ApoE-null mice fed a normal chow diet (FIG. 3A and FIG. 3B). EP80317 did not modulate macrophage accumulation in CD36-null mice (FIG. 3A). CD36 protein expression was reduced to 57 and 27% of controls, respectively, in peritoneal macrophages harvested from HEX- and EP80317-treated ApoE-null mice fed a HFHC diet (FIG. 4).

Figure 5:
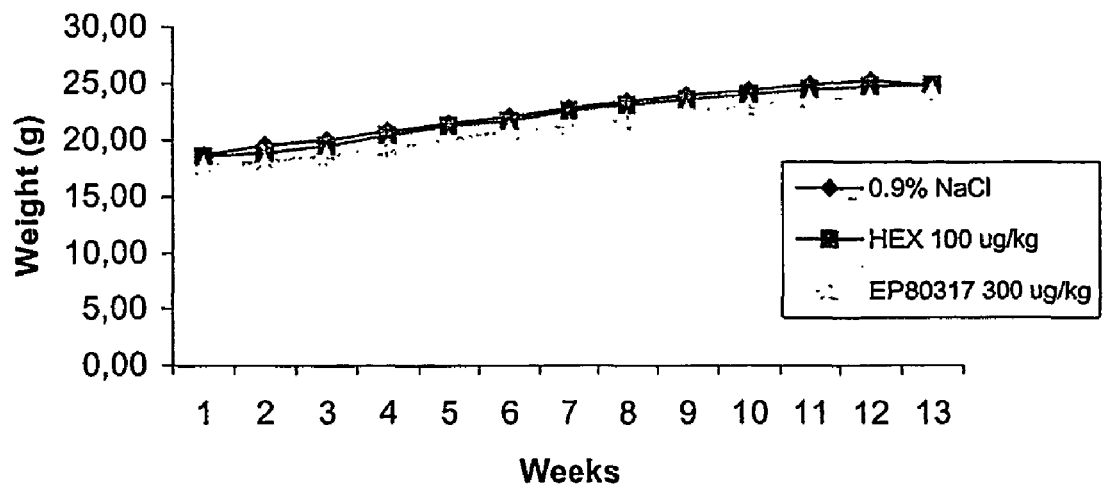
Figure 5:
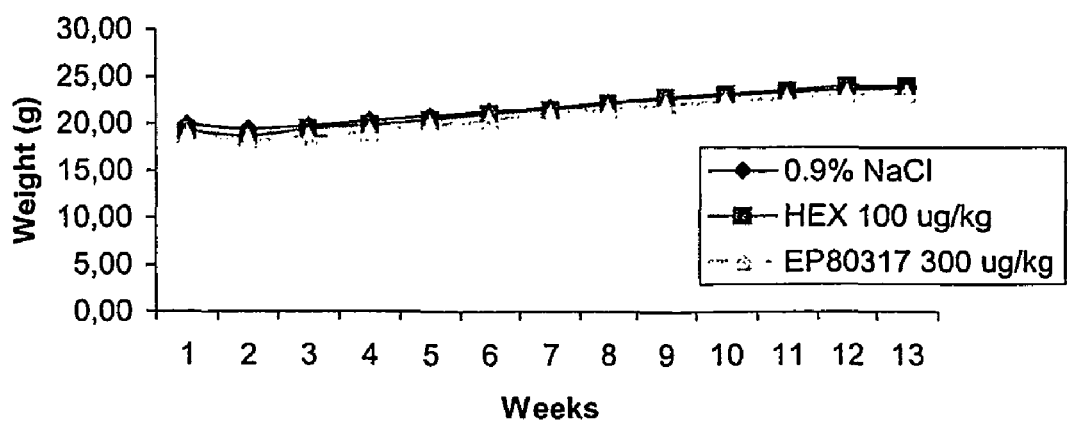
Figure 6:
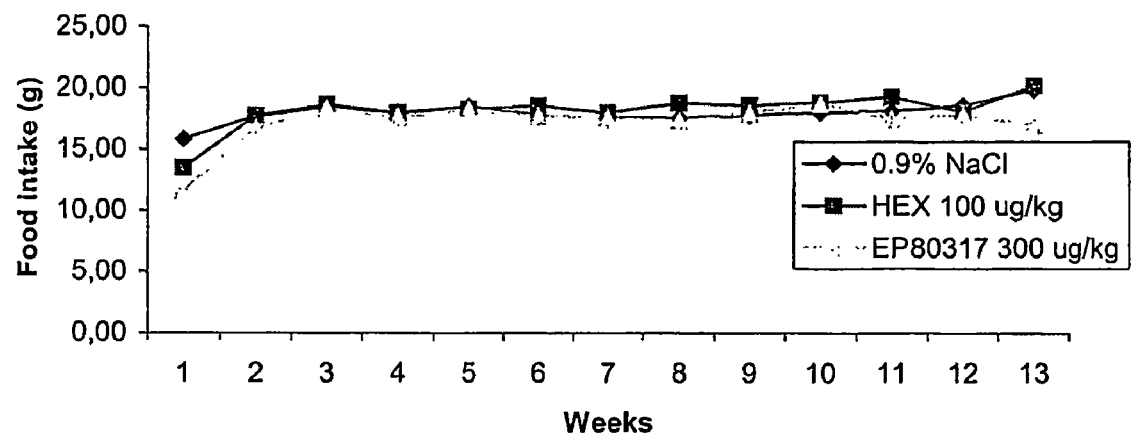
Figure 6:
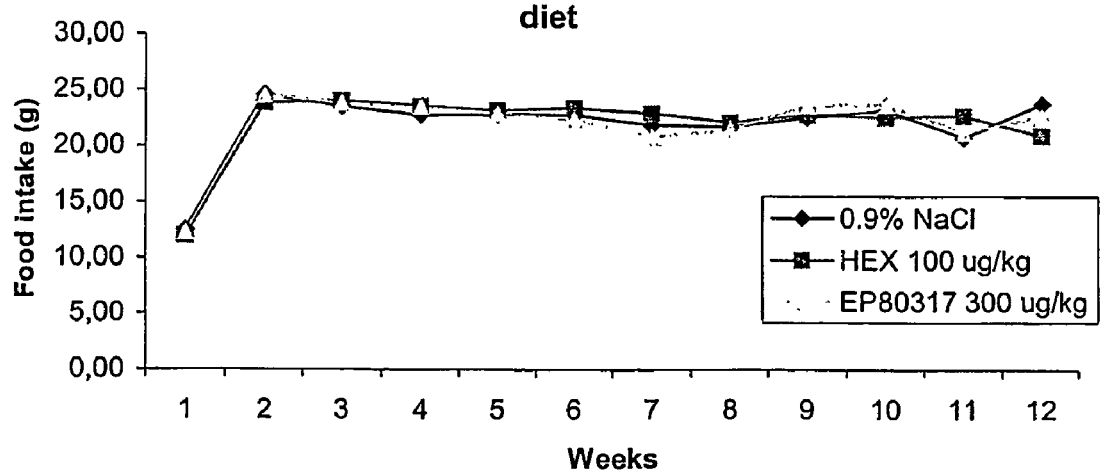

GHRP therapy did not affect the growth curve in ApoE-deficient mice fed a HFHC diet (FIG. 5A) or a normal diet (FIG. 5B), nor the food intake in these mice (FIG. 6A and FIG. 6B).

Discussion

In the present study, we have assessed the contribution of GHRPs in the protective effect against atherosclerosis development. The major findings are:
1) that a prolonged treatment with GHRPs protects mice fed a HFHC diet from developing fatty streak lesions;
2) these protective effects of GHRPs are associated with a favourable modulation in plasma lipids, inasmuch as total plasma cholesterol and non-HDL cholesterol are reduced, and HDL plasma cholesterol is increased, in ApoE-null mice fed a HFHC diet;
3) the atheroprotective effects of GHRPs are associated with a negative modulation of CD36 expression and/or function and increased mRNA levels of LXRα and ABCA1 transporter in macrophages.

These findings suggest that GHRP therapy, through reducing atherosclerosis development, may afford protection against heart attacks and strokes. Thus, GHRPs and their synthetic analogs would appear to be potentially helpful for the treatment or prophylaxis of coronary cardiovascular diseases. For example, they will be useful to prevent hypercholesterolemia and atherosclerosis, thereby reducing the complications associated with the disease. Currently, only few drugs have the capacity to achieve these goals, and these have been associated with potentially severe adverse effects.

EXAMPLE 2

Growth Hormone-Releasing Peptides Modulate the Development of Fatty Streaks

To determine whether GHRPs are able to delay the development or to modulate the regression of fatty streaks, we have used the ApoE-deficient mice to assess the effect of the duration of the treatment with GHRPs on the progression of fatty streaks after the initiation of atherosclerotic lesions induced by a HFHC diet starting at 6 weeks of age.

Methods

Drugs

Solutions of HEX and EP80317 were prepared as described in respect of Example 1 above.

Animals

Male ApoE-null mice (n=35) were housed in cages (less than 5 per cage). After weaning until 4 weeks of age, the mice were fed a normal chow diet and water ad libitum. Starting at 6 weeks of age, the mice were fed a HFHC diet (purchased from Research Diet Inc. (D.12108)). The animals were segregated in 3 groups.

Group 1 (n=10) was subdivided into 2 subgroups, receiving, from 10 to 18 weeks of age (i.e. for 8 weeks), daily injections of EP80317 (300 µg/kg) (n=5) or 0.9% NaCl (n=5).

Group 2 (n=10) was subdivided into 2 subgroups receiving, from 12 to 18 weeks of age (i.e. for 6 weeks), daily injections of EP80317 (300 µg/kg/per day) (n=5) or 0.9% NaCl (n=5).

Group 3 (n=15) was subdivided into 3 subgroups receiving, from 14 to 18 weeks of age (i.e. for 4 weeks), EP80317 (300 µg/kg/per day) (n=5), or hexarelin (100 µg/kg per day) (n=5) or 0.9% NaCl (n=5).

Mice were euthanised at 18 weeks of age. The entire aortas from the heart extending 5-10 mm after bifurcation of the iliac arteries and including the subclavian right and left common carotids were removed, dissected and evaluated for lesion development by en face oil red-O staining and morphometry of scanned images using the software Scion image (Scion Corp., Frederick, Md.).

Results

A significant reduction of the lesion area by 31.3% and 39.2% was observed in the ApoE-null mice aorta following the daily treatment with EP80317 (300 µg/kg) for 6 and 8 weeks, respectively. In addition, a reduction of 36%, although not significant (due to larger variability in the control group), of the lesion area of ApoE-null aortas could be observed following the daily treatment with EP80317 (300 µg/kg) for a period of 4 weeks as compared to controls treated with NaCl.

No significant difference in terms of percentage of the lesion area in the aorta could be observed following the treatment with hexarelin (8%) for a period of 4 weeks as compared to controls treated with 0.9% NaCl.

Discussion

In the present study, we have assessed the contribution of a GHRP derivative, EP80317, not only for its protective effect but also for its curative effect on atherosclerosis lesion development.

EP80317 may delay the development of fatty streaks induced by the HFHC diet. This peptide might also modulate the regression of these fatty streaks in the aortas of ApoE-null mice in which the atherosclerotic process has been induced by a HFHC diet starting at 6 weeks of age.

The invention claimed is:

1. A method of treatment or prophylaxis of atherosclerosis, which method comprises:
treating a patient having (i) atherosclerosis, (ii) two or more risk factors selected from the group consisting of obesity, smoking, hypertension, diabetes mellitus, and family history of premature coronary heart disease, or (iii) a condition selected from the group consisting of very high plasma concentrations of cholesterol and/or triglycerides, hyperlipidemia that is not secondary to underlying disease, and elevated LDL-cholesterol, wherein said patient is treated by administering to the patient, for six or more weeks, one or more Growth Hormone Releasing Peptides (GHRPs), and wherein said administering is effective to treat or prevent atherosclerosis.

2. A method as claimed in claim 1, wherein the patient is at risk of developing atherosclerotic plaques, or cardiovascular disease associated with atherosclerosis, and said administering is effective to prevent development of atherosclerotic plaques, or cardiovascular diseases associated with atherosclerosis.

3. A method as claimed in claim 1, wherein the patient has atherosclerotic plaques.

4. A method as claimed in claim 1, wherein the one or more GHRPs are hexarelin (His-(D)-(Me)Trp-Ala-Trp-(D)-Phe-Lys-NH2, SEQ ID NO: 1) or EP80317 (Haic-(D)-(Me)Trp-(D)-Lys-Trp-(D)-Phe-Lys-NH2, SEQ ID NO: 2).

5. A method as claimed in claim 1, wherein said administering is carried out daily.

6. A method as claimed in claim 1, wherein said administering is carried out for at least eight weeks.

7. A method as claimed in claim 1, wherein the GHRP does not induce secretion of growth hormone.

8. A method as claimed in claim 1, wherein the one or more GHRPs is EP80317 (Haic-(D)-(Me)Trp-(D)-Lys-Trp-(D)-Phe-Lys-NH2, SEQ ID NO: 2).

9. A method for treatment of atherosclerosis, which comprises:
administering to a patient in need of such treatment one or more Growth Hormone Releasing Peptides (GHRPs) that do not induce secretion of growth hormone, wherein said administering is carried out daily using an amount of the one or more GHRPs that is effective to cause reduction of atherosclerotic lesion area or delay of lesion progression.

10. A method as claimed in claim 9, wherein the one or more GHRPs is EP80317 (Haic-(D)-(Me)Trp-(D)-Lys-Trp-(D)-Phe-Lys-NH2, SEQ ID NO: 2).

* * * * *